US006193713B1

(12) United States Patent
Geistert et al.

(10) Patent No.: US 6,193,713 B1
(45) Date of Patent: Feb. 27, 2001

(54) METHOD FOR THE OPERATION OF A HIGH FREQUENCY ABLATION APPARATUS AND APPARATUS FOR THE HIGH FREQUENCY TISSUE ABLATION

(75) Inventors: Wolfgang Geistert, Rheinfelden; Peter Uphoff, Denzlingen, both of (DE)

(73) Assignee: Sulzer Osypka GmbH, Grenzach-Wyhlen (DE)

( * ) Notice: Subject to any disclaimer, the term of this patent is extended or adjusted under 35 U.S.C. 154(b) by 0 days.

(21) Appl. No.: 09/209,157

(22) Filed: Dec. 10, 1998

(30) Foreign Application Priority Data

Dec. 23, 1997 (DE) .............................. 197 57 720

(51) Int. Cl.$^7$ ................................... A61B 18/04
(52) U.S. Cl. ................ 606/34; 606/32; 606/38; 606/41; 606/48; 607/101; 607/102
(58) Field of Search .................. 606/32, 34, 35, 606/38, 41, 42, 46, 48–50; 607/101, 102, 122

(56) References Cited

U.S. PATENT DOCUMENTS

| 4,658,820 | 4/1987 | Klicek ............................. 128/303.14 |
| 4,727,874 | 3/1988 | Bowers et al. .................. 128/303.13 |
| 5,542,916 | * 8/1996 | Hirsch et al. ........................ 604/22 |
| 5,630,837 | 5/1997 | Crowley .................................. 601/2 |
| 5,693,078 | 12/1997 | Desai et al. .......................... 607/102 |
| 5,697,909 | * 12/1997 | Eggers et al. ....................... 604/114 |
| 5,772,659 | * 6/1998 | Becker et al. ......................... 606/34 |
| 5,837,001 | * 11/1998 | Mackey .................................. 607/102 |

FOREIGN PATENT DOCUMENTS

| 35 31 576 C2 | 5/1986 | (DE) ................. A61B/17/39 |
| WO 96/00036 | 1/1996 | (WO) ............................ A61B/17/36 |
| WO 96/39086 | 12/1996 | (WO) ............................ A61B/17/39 |
| WO 96/39088 | 12/1996 | (WO) ............................ A61B/17/39 |
| WO 97/20510 | 6/1997 | (WO) ............................ A61B/17/39 |
| WO 97/21387 | 6/1997 | (WO) ............................ A61B/17/39 |
| WO 97/40760 | 11/1997 | (WO) ............................ A61B/17/39 |

OTHER PUBLICATIONS

English Translation of European Search Report, dated Apr. 26, 1999, relating to European Patent Application No. 98 120 431.6.
German Patent Application No. 197 57 720.2 Search Report, dated Jun. 29, 1998.
English Translation of German Search Report, dated Jun. 29, 1998, relating to German Patent Application No. 197 57 720.2.

* cited by examiner

Primary Examiner—Linda C. M. Dvorak
Assistant Examiner—David M. Ruddy
(74) Attorney, Agent, or Firm—Fitch, Even, Tabin & Flannery

(57) ABSTRACT

A method is described for the operation of a radiofrequency ablation instrument comprising a radiofrequency energy source having a plurality of regulatable outputs, with a plurality of electrodes being connectable to its outputs. A respective power value and/or current value representative of the power and/or the current transmitted by the radiofrequency energy source is detected for each output. The voltage delivered from the radiofrequency energy source is regulated in dependence on the detected power value and/or current value in such a way that the latter corresponds substantially to a predetermined power value and/or current value. A predetermined phrase relationship is in each case maintained between the currents or between the voltages at the outputs of the radiofrequency energy source. Furthermore, a corresponding apparatus is described.

22 Claims, 2 Drawing Sheets

METHOD FOR THE OPERATION OF A HIGH FREQUENCY ABLATION APPARATUS AND APPARATUS FOR THE HIGH FREQUENCY TISSUE ABLATION

The present invention relates to a method for the operation of a high frequency ablation instrument comprising a radiofrequency energy source having a plurality of regulatable outputs, with a plurality of electrodes being connected to its outputs. Furthermore, the invention is directed to an instrument for high frequency tissue ablation.

Ablation instruments of this kind are, for example, used for the treatment of cardiac irregularity or disordered action of the heart. For this purpose an ablation catheter having one or more electrodes is connected to a radiofrequency energy source and is, for example, introduced via a blood vessel into the interior of the heart. The electrodes provided at the end of the catheter are positioned at the desired location at the inner or outer surface of the heart, whereupon the regions standing in contact with the electrodes are thermally obliterated by the supply of radiofrequency energy.

The electrical characteristics of the treated heart tissue are so changed through the lesions which are produced in this manner that cardiac irregularities which are present are removed.

Catheters with only one electrode are poorly suited for certain types of cardiac irregularities, for which larger areas of tissue have to be obliterated, since the sequence of a plurality of point-like lesions that is required with the heart beating is generally only inadequate and only possible with a large expenditure of time. For the obliteration of larger areas of tissue, catheters having a plurality of electrodes can be used. In this arrangement it is advantageous if the energy yield for each catheter electrode can be individually adjusted so that, for example, the ideal temperature acting in the tissue can be set for each catheter electrode, despite different cooling conditions in the different electrodes, and also despite different load resistances for each catheter electrode.

The individual catheter electrodes normally cooperate with a large area electrode contacting the body of the patient to be treated, the so-called indifferent electrode, so that with an energy supply to the catheter electrodes, current in each case flows from the catheter electrodes through the body of the patient to the indifferent electrode. Since the current density is highest directly at the transition between the catheter electrodes and the tissues to be treated, as a result of the small area of the catheter electrodes, the temperature in this region is sufficiently high, with adequate energy supply, that the desired lesions are produced.

When using catheters with a plurality of electrodes, the following problem arises: Since, in dependence on the requirement, different temperatures can be necessary at different catheter electrodes, or different energies can be necessary to achieve a specific temperature, and since the load resistances which become active at the electrodes can be different, the energy yield via the individual catheter electrodes must be individually set. This leads to different voltage values and current values being necessary at the different catheter electrodes. In particular, when the catheter outputs have low output resistances, compensation currents arise between electrodes to which different voltage values are applied or with phase shifts between the output voltages. These compensation currents are currents which flow, instead of to the indifferent electrode, to another catheter electrode at which a voltage is present which differs from the voltage at the electrode from which the current emerges. If a high potential difference exists between the two catheter electrodes, then the compensation current flowing into the other electrode can lead to undesirably high current densities at this electrode, which in turn bring about undesired coagulations at this electrode. This effect is particularly notable at electrodes at which no energy transmission or only a small energy transmission is desired.

BRIEF SUMMARY OF THE INVENTION

The object of the invention is to design an instrument and a method of the initially named kind so that compensation currents between the outputs or between electrodes connected to the outputs are largely avoided. Furthermore, a continuous energy delivery should be possible. The instrument should have a high degree of efficiency and also the circuit complexity should be as low as possible.

Starting from a method of the initially named kind, the part of the object relating to the method is satisfied in that a respective power value and/or current value representative of the power and/or the current transmitted by the radiofrequency energy source is detected for each output; in that the voltage transmitted from the radiofrequency energy source is so regulated in dependence on the detected power value and/or current value that the latter corresponds substantially to a predetermined power value and/or current value; and in that a predetermined phase relationship is in each case maintained between the currents or between the voltages at the outputs of the radiofrequency energy source.

The part of the object relating to the apparatus is satisfied in accordance with the invention by an instrument of the initially named kind with at least one measurement element for detecting power values and/or current values representative for the power and/or current delivered at the respective outputs, and by at least one regulating element connected to the measurement element for the regulation of the voltage delivered by the radiofrequency energy source in dependence on the detected power value and/or current value applied to an actual value input of the regulating element, and on a preset power value and/or current value applied to a desired value input of the regulating element, with the currents or voltages at the outputs of the radiofrequency energy source each having a predetermined phase relationship to one another.

The apparatus of the invention is thus so designed that its outputs have the behavior of a current or power source. In this way compensatory currents which would, for example, flow from an electrode with a higher voltage to an electrode with a lower voltage and lead to a feedback into this electrode are avoided. This feedback would lead to a situation in which, in an extreme case, a current of higher magnitude undesirably flows through the compensatory current to this electrode, which brings about an undesired coagulation at this electrode. For example, under some circumstances, the compensation current can be subtracted from the suppressed output current of the affected electrode, which can lead to a situation in which the direction of action of the current flowing through the affected electrode is reversed.

Through the current or power regulation in accordance with the invention, this deviation in the desired value is directly counteracted by follow-up regulation, for example, by an increase of the output voltage, so that the desired current again flows through the electrode.

In accordance with a preferred embodiment of the invention, the rf-energy source comprises at least one regulatable DC voltage source, which consists, for example, of a non-regulated DC voltage source and a voltage regulator, and at least one switching stage connected to the DC voltage source, with the or each switching stage being controlled by an in particular periodic switching signal for the generation of the rf output voltage, and with the voltage transmitted by the DC voltage source being regulated for the regulation of the voltage transmitted by the rf energy source. In this manner a particularly simple and cost favorable design of an instrument formed in accordance with the invention is possible. the switching signal thereby normally consists of rectangular pulses, with the frequency of the switching signal typically lying in the range from 300 to 1000 kHz.

In a further advantageous embodiment of the invention, the power transmitted by the DC voltage source and/or the current transmitted by the DC voltage source are detected, so that the power and/or current detection takes place at the primary side of the rf-energy source. For this purpose the measuring element for detecting the power and/or the current transmitted by the rf-energy source is arranged between the DC voltage source and the switching stage, or directly inside the DC voltage source. In the detection of the current and/or of the power at the primary side of the rf-energy source, the transformation factor and degree of efficiency of the switching stages and also of any possibly further present elements, such as for example a voltage regulator which is present, must be taken into account in the determination of the current and/or of the power.

Through the detection of the current and/or of the power at the primary side of the rf-energy source, it is possible to avoid additional switching elements at the secondary side, which could lead to undesirable patient dissipation currents and to rf-leakage currents. Furthermore, the detection of the power and/or of the current at the primary side is associated with substantially less hardware cost and complexity than at the secondary side.

Fundamentally, it is however, also possible for the power and/or the current to be detected between the switching stage and the output of the rf-energy source, i.e. at the secondary side of the rf-energy source.

In accordance with a further preferred embodiment of the invention, a switching stage and a measurement element are associated with each output of the rf-energy source. In this manner it is ensured that each electrode which is connected to an output can be set individually and ideally.

The switching stage preferably includes at least one transformer, through which the primary and secondary side of the rf-energy source are coupled to one another, with at least one switch, which is in particular formed as a transistor being provided at the primary side. If the current detection and/or the power detection takes place at the primary side of the RF energy source and thus of the transformer, then it is possible, in the event that the switching stage operates substantially linearly over a wide operating range, for this detection to take place through calculation with the following formulae:

$$P_{HF}=(P_{DC}-P_{DC0})\times \eta$$

$$P_L=(R_{DC}-R_{DC0})\times k,$$

with $P_{HF}$ being the rf-output power at the secondary side, $P_{DC}$ the supply power at the primary side, $P_{DC0}$ the supply power without RF output, $\eta$ the degree of efficiency, $R_L$ the load resistance at the secondary side, $R_{DC}$ the detectable DC resistance at the primary side, $R_{DC0}$ the DC current resistance offset and k a circuit specific, resistance transformation factor.

Fundamentally, it is however also possible for the determination of the secondary values to take place from the primary values via tables or a combination of calculations and tables. Instead of transistors any other desired switches, for example tubes, can be used, which can follow the required switching frequency of the switching signal of, for example, 300 to 1000 kHz.

In accordance with a further advantageous embodiment of the invention, the DC voltage sources deliver substantially the same maximum voltage value, with all outputs in particular being fed from a unitary DC voltage source. The use of a unitary maximum voltage value for all outputs brings about the following advantage in accordance with the invention. If a high compensation current arises as a result of a high potential difference between two catheter electrodes, then, as already described, the voltage transmitted by the associated DC voltage source is increased through the regulation of the impressed output current affected by the compensation current until the deviation from the desired value brought about by the compensation current has been cancelled. In the extreme case the circuit goes into saturation, because the maximum value of the DC voltage source restricts the control range. If all DC voltage sources have the same maximum voltage value, then in the extreme case the voltage sources associated with the two affected electrodes deliver the same voltage, so that as a result of the same potential, no compensation current can flow.

The predetermined power values and/or current values are predetermined by a control, which can in particular be designed as a temperature regulation. For this purpose temperature sensitive sensors are provided in the region of the outputs of the rf-energy source, in particular in the region of the electrodes, and are connected to the control circuit. The desired power values and/or current values which are applied to the regulating element are determined in dependence on the temperature values measured by the sensors through the control circuit for each regulating element. It is fundamentally also possible to use other suitable measurement parameters for the regulation. For example, a regulation in accordance with the absolute impedance value and/or in accordance with changes of the impedance value can be used instead of or in addition to the temperature regulation.

Further preferred embodiments are set forth in the subordinate claims.

BRIEF DESCRIPTION OF THE DRAWINGS

The invention will subsequently be described in more detail with reference to embodiments and to the drawings in which are shown.

Figure 1:
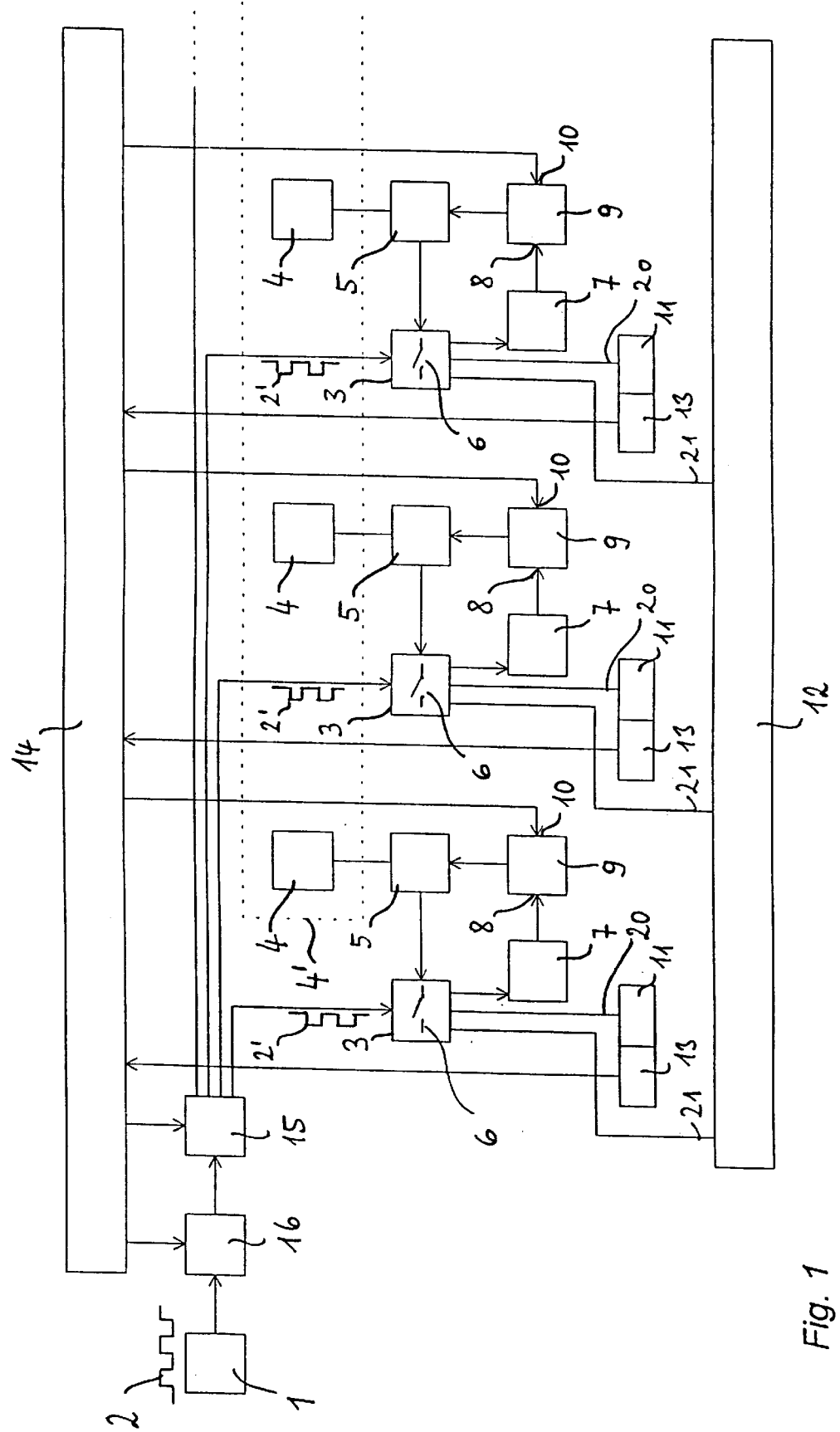
FIG. 1 a block circuit diagram of an embodiment of an apparatus designed in accordance with the invention, FIG. 2 a schematic illustration of a single-ended switching stage with a regulatable DC voltage source and a current flow monitoring element, such as can be used in an apparatus in accordance with FIG. 1, FIG. 3 a schematic representation of a push-pull switching stage with a regulatable voltage source and a current flow monitoring element, FIG. 4 a schematic representation of a half-bridge switching stage with a regulatable voltage source and current flow monitoring element, and FIG. 5 a schematic illustration of a full-bridge switching stage with a regulatable voltage source and a current flow monitoring element.

The apparatus shown in FIG. 1 includes a cycle or clock generator 1, which produces a periodic, rectangular switching signal 2 for a plurality of switching stages 3. A DC voltage source 4 is associated with each switching stage 3 and supplies the switching stage 3 with a variable voltage via a respective voltage regulator 5. The DC voltage sources 4 each deliver the same voltage value so that instead of different voltage sources 4 a common voltage source 4' can also be used, as is shown in broken lines in FIG. 1.

The switching stages 3 each contain at least one schematically indicated switch 6, which is, for example, formed as a transistor or tube and is controlled, i.e. opened and closed by the switching signal 2', which is applied to the respective switching stage 3. Through the controlling of the switch, the DC voltage applied from the voltage regulator 5 to the switch 6 is chopped up, whereby the RF output voltage of the switching stage 3 is produced. Thus, the output voltage of the respective switching stage 3 is determined by the voltage delivered by the voltage regulator 5 to the switching stage 3.

The current flowing via the switch 6, or the corresponding power, is detected for each switching stage 3 by a measurement element 7 in each case and supplied to the actual value input 8 of a regulating element 9. The measurement element 7 can in this arrangement, for example, also be arranged in the path between the voltage regulator 5 and the switching stage 3, or in the path between the DC voltage source 4 and the voltage regulator 5. At these points the current or the power is thus measured at the primary side of the switching stage 3, whereby the occurrence of additional dissipatory currents through additional circuit elements on the secondary side is avoided.

The regulating element 9 sets the current detected by the measurement element 7 or the power detected by the measurement element 7 in accordance with a desired value applied to a desired value input 10 of the regulating element and controls the voltage regulator 5, so that the supply voltage for the respective switching stage 3 is regulated in such a way that the detected current of the detected power is kept constant.

At the secondary sides of the switching stages 3, there are formed respective outputs 20, 21 of the rf-energy source, which are each connected, on the one hand, to a respective catheter electrode 11 and, on the other hand, to a common, indifferent electrode 12.

A respective temperature sensitive sensor 13 is arranged in the region of each electrode 11 and is connected to a control circuit 14 for the transmission of an output signal dependent on the measured temperature. The control circuit 14 in turn delivers the desired value for the regulating elements 10 in dependence on the measured temperature and also possibly in dependence on a preset desired temperature.

Whereas the switching signals 2', which are applied in the previously described circuit to the switching stages 3, are each in phase, it is possible via a phase shifter 15 connected after the clock generator 1 to intentionally shift the phase position of the switching signals 2 relative to one another, whereby defined compensatory currents can be produced between the electrodes 11. These compensatory currents flow at the surface of the tissue and can serve to close lesion gaps between the catheter electrodes 11. Furthermore, an interrupter circuit 16 is arranged between the clock generator 1 and the phase shifter 15, with which the switching signals 2 produced by the clock generator 1 can be regularly interrupted in order to produce a pulsing of the output power. In this way the lesion profile can be advantageously controlled, with both the duration and also the frequency of the interruptions produced by the interruption circuit 16 being capable of being set.

Figure 2:
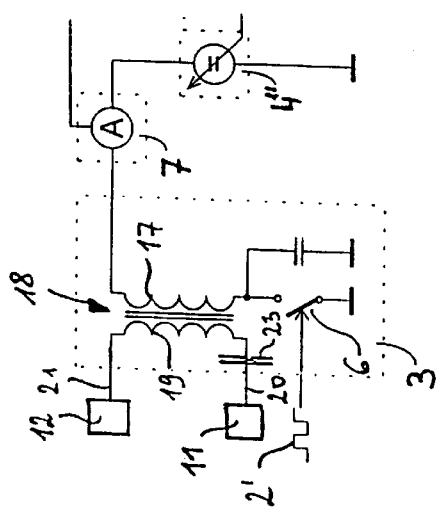

FIG. 2 shows a design of the switching stage 3 as a single ended switching stage and, for the sake of easier comprehension, some of the components already shown in FIG. 1 and connected to the switching stage 3 are likewise shown in FIG. 2.

The switch 6 of the switching stage 3 is connected in series with the primary winding 17 of a transformer 18, with the other end of the primary winding 17 being connected to the measurement element 7. The secondary winding 19 of the transformer is connected at its one terminal to the catheter electrode 11, normally via a capacitor 23, and with its other terminal to the indifferent electrode 12.

The DC voltage source 4 shown in FIG. 1 and also the voltage regulator 5 are combined in each of FIGS. 2 to 5 into a regulated voltage source 4".

As can be seen from FIG. 2, the voltage delivered from the DC voltage source 4" is chopped up by the control of the switch 6 through the switching signal 2' and is transmitted via the transformer 18 from the primary winding 17 to the secondary winding 19. The current which is thereby induced flows via the catheter electrode 11 into the tissue to the indifferent electrode 12, whereby the tissue is coagulated in the region of the catheter electrode 11.

Figure 3:
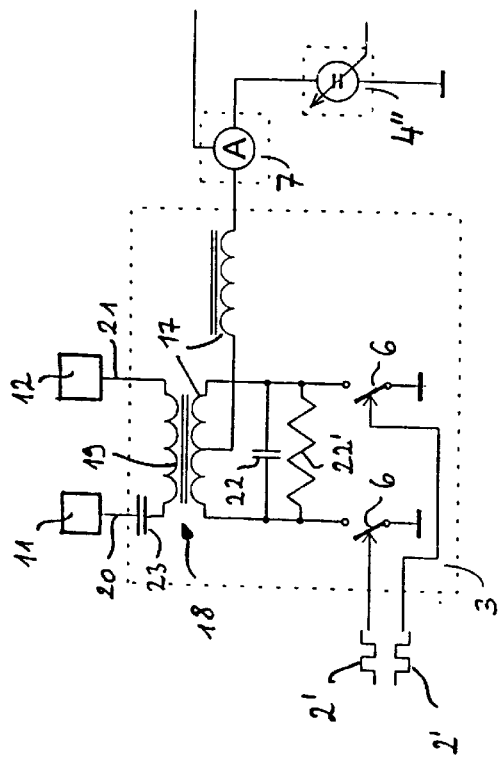
Figure 5:
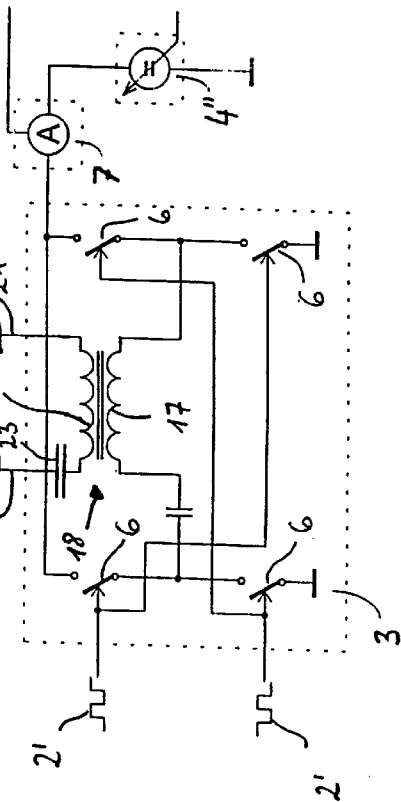
Figure 4:
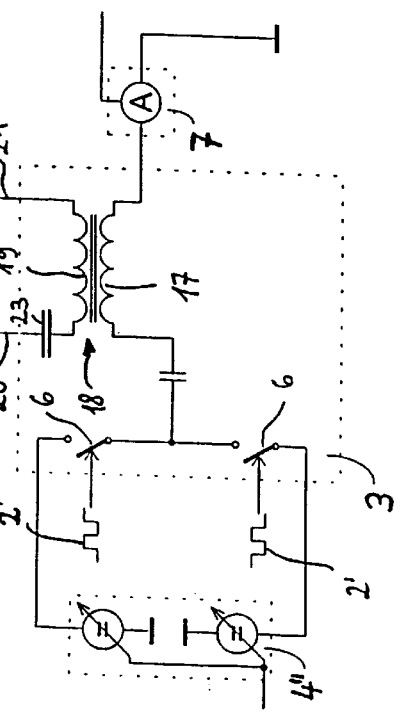

Whereas the single ended switching stage shown in FIG. 2 is controlled solely by a single switching signal 2', the switching stages shown in FIGS. 3 to 5 are each controlled by two switching signals 2' of opposite phase. As in the single-ended switching stage of FIG. 2, the secondary winding 19 of the transformer 18 is connected in each of the switching stages in accordance with FIGS. 3 to 5 to the catheter electrode 11 and to the indifferent electrode 12, so that the same effect can be achieved with these switching stages as with the single ended switching stage in accordance with FIG. 2.

The manner of operation of an apparatus formed in accordance with the invention will be described again in more detail in the following with reference to the Figures.

A switching signal 2 is generated by the clock generator 1, which can be interrupted timewise by the interrupter circuit 16 and can be converted by the phase shifter 15 into switching signals 2' with different phase positions.

The switching signals 2' respectively control the switch or switches 6 at the switching stage 3, so that the DC voltage delivered by the DC voltage source 4, as set via the voltage regulator 5 and present at the switching stage 3, is converted into an AC voltage. The current flowing at the primary side is measured by the measurement element 7 and passed on to the regulating element 9, which so controls the voltage regulator 5 on the basis of a desired value for power or current applied to the control circuit 14 that the current or power detected remain constant.

At the secondary side the switching stage 3 is connected via the outputs 20, 21 of the RF energy source to the catheter electrode 11 and also to the indifferent electrode 12, so that the tissue contacting the catheter electrode 11 is heated and denatured as a result of the high current density arising at this location.

The temperature prevailing in the region of the catheter electrode 11 is measured by the sensor 13 and transmitted to the control circuit 14, through which a corresponding desired value is applied to the regulating element 9.

If a potential drop exists between two adjacently disposed catheter electrodes 11, then it is possible for a compensation current to flow from the electrode 11 with the higher voltage to the electrode 11 with the lower voltage. Since this compensation current is superimposed on the impressed output current of the electrode 11 with the lower voltage, the regulating element 9 controls the voltage regulator 5, after detection of the resulting current value by the measurement element 7, in such a way that the voltage applied to the switching stage 3 is subjected to follow-up regulation and the desired value of the current or the power is set again.

In the extreme case the voltage applied to the switching stage 3 will be regulated up to the saturation limit, with it being ensured, through the use of a unitary voltage source 4', that in this extreme case the same voltage is applied both to the electrode 11 delivery the compensation current and also to the electrode 11 receiving the compensation current, so that no compensation current can flow between these two electrodes 11.

While it has previously been described that a temperature sensor is associated with each catheter electrode, it is basically also possible to provide a plurality of sensors for each electrode or a common reference sensor for a plurality of electrodes or no sensor for some of the electrodes or all of the electrodes.

The use of the described switching stages is of advantage because these have a high degree of efficiency, since the power losses via the switches are low.

In order to further reduce the power feedback, it can be possible to switch all the switches into the open position if the corresponding switching stage is controlled by a supply voltage of 0 Volt.

Undesired compensation currents can also be prevented in an advantageous further development, in which no circuit elements are used, which would permit a significant passive current impression, such as is the case, for example, with relief networks. Furthermore, preferred switching elements are provided which reduce the harmonic content of the output voltage. The operation of apparatus being operated in the vicinity can be disturbed by harmonics, so that the amplitudes of the harmonic waves can be reduced by corresponding circuit elements, for example, capacitors 22 (FIG. 3) connected in parallel to the primary winding of the output transformer or a capacitor-resistor combination 22, 22' (FIG. 3).

It is fundamentally also possible, instead of using a common, indifferent electrode, to provide further electrodes, for example, on the same catheter or on another catheter, which serve as the counterpole to the described catheter electrodes. In addition, the circuit can be of modular design, so that, for example, the control circuit of each individual electrode can be formed by a separate module.

It can also be sensible, for all medical applications in particular, to provide the rf-energy source with a voltage control characteristic. In this respect it can be sensible to provide regulating elements both for the current regulation and also for the voltage regulation, with a determination advantageously being made through the load conditions, as to which of the two regulations is active. The measurement of the voltage value required for the voltage regulation can in turn selectively take place either at the primary side or at the secondary side of the switching stages.

What is claimed is:

1. Method of operating a radiofrequency ablation instrument comprising a radiofrequency energy source having a plurality of regulatable outputs, with a plurality of electrodes being connectable to its outputs, at least one regulatable DC voltage source and at least one switching stare connected to the DC voltage source, the method comprising controlling for the generation of the radiofrequency output voltage, at the or each switching stage by a periodic switching signal, and regulating the voltage transmitted from the DC voltage source for the regulation of the voltage delivered by the radiofrequency energy source, detecting for each output a respective power value and/or current value representative of the power and/or the current transmitted by the radiofrequency energy source;

regulating a voltage transmitted from the radiofrequency energy source in dependence on the detected power value and/or current value such that the latter corresponds substantially to a predetermined power value and/or current value; and maintaining a predetermined phase relationship in each case between the currents or between the voltages at the outputs of the radiofrequency energy source.

2. A method in accordance with claim 1, wherein the power transmitted from the DC voltage source and/or the current transmitted by the DC voltage source is detected at the output side of the radiofrequency energy source.

3. A method in accordance with claim 1, wherein the power and/or the current is detected between the switching stage and the output of the radiofrequency energy source.

4. A method in accordance with claim 1, wherein a switching stage is associated with each output of the radiofrequency energy source and at least some of the switching stages are controlled by phase-synchronized switching signals.

5. A method in accordance with claim 1, wherein a switching stage is associated with each output of the radiofrequency energy source and at least some of the switching stages are controlled by mutually phase-shifted switching signals.

6. A method in accordance with claim 5, wherein the phase-shift of the switching signals is adjustable.

7. A method in accordance with claim 1, comprising interrupting the switching signals at intervals, for time sections of the same length or of different lengths.

8. A method in accordance with claim 7, wherein the time points and/or the frequency and/or the duration of the interruptions are adjustable.

9. A method in accordance with claim 1, wherein the DC voltage sources deliver at least substantially the same maximum voltage value.

10. A method in accordance with claim 1, comprising measuring temperature values and/or absolute impedance values and/or changes of impedance in the region of electrodes connected to the outputs, and determining the predetermined power values and/or current values in dependence on the measured values.

11. Apparatus for the high frequency ablation of tissue comprising a radiofrequency energy source having a plurality of regulatable outputs, with a plurality of electrodes being connectable to its outputs, at least one regulatable DC voltage source, at least one switching stage connected to the DC voltage source and a cycle generator which transmits a periodic switching signal, for controlling the switching stage, at least one measurement element for detecting power values and/or current values representative of the power and/or current delivered at the respective outputs, at least one regulating element connected to the measurement element for the regulation of the voltage delivered by the radiofrequency energy source in dependence on the detected power value and/or current value applied to an actual value input of the regulating element, and on a preset power value and/or current value applied to a desired value input of the regulating element, and a phase controller for maintaining a predetermined phase relationship in each case between the currents or between the voltages at the outputs of the radiofrequency energy source.

12. Apparatus in accordance with claim 11, wherein the measurement element is arranged for the detection of the power and/or of the current delivered by the radiofrequency energy source between the DC voltage source and the switching stage, or within the DC voltage source or the switching stage.

13. Apparatus in accordance with claim 11, wherein the measurement element for the detection of the power and/or of the current delivered by the radiofrequency energy source is arranged between the switching stage and the output of the radiofrequency energy source.

14. Apparatus in accordance with claim 11, wherein a switching stage and a measurement element are associated with each output of the radiofrequency energy source.

15. Apparatus in accordance with claim 11, wherein the radiofrequency energy source has a primary and a secondary side and the switching stage includes at least one transformer, through which the primary and the secondary side of the radiofrequency energy source are coupled to one another, with at least one switch being provided at the primary side.

16. Apparatus in accordance with claim 11, comprising a phase shifter, with which the phase position of the switching signals, which control the switching stages, can be mutually shifted.

17. Apparatus in accordance with claim 11, comprising an interruption element for the selectively adjustable interruption of the switching signals.

18. Apparatus in accordance with claim 11, wherein the DC voltage sources deliver at least substantially the same maximum potential value.

19. Apparatus in accordance with claim 11, wherein the switching stages are formed as single-ended switching stages, as push-pull switching stages, as half-bridge switching stages or as full-bridge switching stages.

20. Apparatus in accordance with claim 11, wherein temperature sensitive sensors and/or impedance measuring elements are provided in the region of electrodes connected to the outputs; the sensors or the impedance measuring elements are connected to a control circuit for the determination of the predetermined power values and/or current values in dependence on the measured temperature values or on the measured absolute impedance, or on the measured changes in impedance; and the control circuit is connected to the regulating element.

21. High frequency ablation catheter having an instrument in accordance with claim 11 and a plurality of electrodes, which are respectively connected to the outputs of the radiofrequency energy source.

22. Catheter in accordance with claim 21, wherein in each case precisely one electrode is connected with precisely one output.

* * * * *